US006864056B1

(12) United States Patent
Davies et al.

(10) Patent No.: US 6,864,056 B1
(45) Date of Patent: Mar. 8, 2005

(54) METHOD FOR DETECTING RIBOSOME INACTIVATING PROTEINS

(75) Inventors: Julian E. Davies, Vancouver (CA); Richard Kao, Surrey (CA); Ronald Young, Columbia, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 10 days.

(21) Appl. No.: 09/911,048

(22) Filed: Jul. 23, 2001

Related U.S. Application Data

(60) Provisional application No. 60/222,002, filed on Jul. 31, 2000.

(51) Int. Cl.[7] .......................... C12Q 1/68; C12P 19/34; C07H 21/02; C07H 21/04; C07H 21/00
(52) U.S. Cl. ....................... 435/6; 435/91.1; 536/23.1; 536/24.3; 536/24.33; 536/25.3
(58) Field of Search ........................... 435/6, 91.1, 183; 436/94; 536/23.1, 24.3, 24.33, 25.3, 25.32

(56) References Cited

U.S. PATENT DOCUMENTS 5,538,871 A * 7/1996 Nuovo et al. .............. 435/91.2
6,034,233 A * 3/2000 Ecker et al. ................ 536/24.5

OTHER PUBLICATIONS

Kao et al., Novel rapid method for the detection of ricin A–chain and related ribotoxins. Proceedings of the ERDEC Scientific Conference on Chemical and Biological Defense Research, pp. 483–491, on Nov. 17–20, 1998, MD, United States.*

Zamboni et al., High–pressure–liquid–chromatographic and fluorimetric methods for the determination of adenine released from ribosomes by ricin and gelonin. Biochem. J., 259, 639–643, 1989.*

Szewczak et al., The conformation of the sarcin/ricin loop from 28S ribosomal RNA. Proc. Natl. Acad. Sci. USA, 90, 9581–9585, Oct. 1993.*

Brigotti et al., A rapid and sensitive method to measure the enzymatic activity of ribosome–inactivating proteins. Nucleic Acids Res., 26, 4306–4307, 1998.*

* cited by examiner

*Primary Examiner*—Gary Benzion
*Assistant Examiner*—Frank W Lu
(74) *Attorney, Agent, or Firm*—Ulysses John Biffoni

(57) ABSTRACT

The present invention concerns a method for detecting the presence of a ribosome inactivating protein in a sample. The method comprises contacting a sample suspected of containing a ribosome inactivating protein with a 2'-O-methylated oligonucleotide substrate having a $GA_xGA$ tetraloop wherein "$A_x$" is a deoxyribonucleoside comprising a fluorescent adenine derivative or analog base capable of emitting a fluorescence when released from the nucleoside, "$A_x$", and detecting the presence of the fluorescent adenine derivative or analog base released from the tetraloop as an indication of the presence of the ribosome inactivating protein in the sample. The present invention is also directed to an assay kit and a reagent useful for carrying out the steps of the above method.

8 Claims, 6 Drawing Sheets

SEQUENCE LISTING

<160> NUMBER OF SEQ ID NOS: 1

<210> SEQ ID NO 1
<211> LENGTH: 19
<212> TYPE: RNA
<213> ORGANISM: Artificial Sequence
<220> FEATURE:
<221> NAME/KEY: misc_feature
<222> LOCATION: 12
<223> OTHER INFORMATION: n=adenine, adenine analog, adenine derivative; sequence is synthetic

<400> SEQUENCE: 1
uuuuucgcgc gngagcgcg         19

METHOD FOR DETECTING RIBOSOME INACTIVATING PROTEINS

RELATED APPLICATION

The present Application claims the priority of U.S. Provisional Application Ser. No. 60/222,002 filed Jul. 31, 2000, which is fully incorporated herein by reference.

GOVERNMENTAL INTEREST

The invention described herein may be manufactured, licensed, and used by or for the U.S. Government.

FIELD OF THE INVENTION

The present invention relates to cytotoxins, more particularly to methods for detecting cytotoxins including ribosome inactivating proteins or ribotoxins in a sample.

BACKGROUND OF THE INVENTION

Ribosome inactivating proteins, which are toxic to animals and humans (RIPS, also known as ribotoxins), are generally derived from plant proteins. RIPs act by catalytically inactivating ribosomes in eukaryotic cells which inhibit protein synthesis and cause cellular destruction. RIPs are generally divided into two classes, the Type 1 RIP and the Type 2 RIP. There is significant amino acid sequence homology between members of Type 1 and Type 2 RIPs and bacterial Shiga and Shiga-like toxins, however, the Type 2 RIPs and the bacterial Shiga and Shiga-like toxins have similar mechanisms of action.

Type 2 RIPs are composed of two polypeptide chains: an A-chain, and a lectin-like protein referred to as a B-chain. The A-chain and B-chain are covalently attached to each other via a disulfide bond. The B-chain has a high affinity for cell surface moieties, and is capable of reversibly binding to a specific receptor on the cell membrane. Once bound to the specific receptor, the uptake of the A-chain into the cell is achieved through endocytosis.

Once inside the cell, the A-chain, which is an N-glycosidase, operates to enzymatically remove an adenine base at a specific site on the 28S ribosomal RNA (r-RNA). The resulting depurination action prevents an elongation factor from binding to the r-RNA, thus inhibiting protein synthesis. For these reasons, Type 2 RIPs are very potent cytotoxins and animal poisons even at extremely low concentrations. The best known Type 2 RIP is ricin which has a median lethal dose ($LD_{50}$) of about 3 $\mu$g/kg.

Type 1 RIPs are typically composed of a single polypeptide chain that is equivalent in activity to the A-chain of Type 2 RIPs. Lacking analogs of the B-chain, Type 1 RIPs are minimally toxic to cells with intact membranes. However, in absence of cell membranes, Type 1 RIPs retain significant potency in inhibiting ribosomes and protein synthesis.

Type 1 and Type 2 RIPs may be derived from a variety of dicot and monocot plants, and thus can be found in many places. They are often abundant in seeds, roots and the latex of the plant. The exact function of RIPs in vivo is unclear. It has been theorized that they act as antiviral or antifungal agents. Type 2 RIPs possess the catalytically active A-chain, and retain depurination activity in ribosomes. Type 2 RIPs generally target a specific nucleotide sequence called the G(A)GA tetraloop which is typically found in the large ribosomal RNA of eukaryotic cells, and enzymatically remove the first adenine base, (A), from the tetraloop nucleotide sequence. For example, in rat liver cells, the A-chain has been shown to remove a specific adenine base through cleavage of the glycosidic bond of adenine 4323 from 28S ribosomal RNA.

Type 2 RIPs including ricin have been studied and tested for use in weapon systems. Their extreme toxicity make them potential candidates for use or deployment during warfare or acts of terrorism. In the event that Type 2 RIPs are ever deployed, part of the initial defense includes the rapid and accurate detection of RIPs especially at the submicrogram levels of concentration. Currently available military systems for detecting and identifying RIPs are laboratory based, requiring sophisticated and expensive equipment. Therefore, such systems are of limited practical use in the field.

Accordingly, there is a need to develop methods for rapidly detecting RIPs particularly Type 2 RIPs and related ribotoxins, including, but not limited to, ricin toxin A-chain (RTA), ricin, abrin, gelonin, SLT-1, momordin, which would permit protective measures or countermeasures to be quickly implemented in the event of an attack with weapons employing the same. There is also a need to provide an assay preferably in the form of a field kit that is sturdy, portable, rapidly deployable and simple to use. Moreover, the demand for methods and assays capable of rapidly detecting RIPs has applications beyond those of the military such as in the pharmaceutical, medical, food and public safety industries, and the like.

SUMMARY OF THE INVENTION

The present invention is generally directed to methods and reagents for rapidly detecting RIPs particularly Type 2 RIPs and bacterial ribotoxins with mechanisms of action similar to those found in Type 2 RIPs, and to an assay kit for conducting the same.

In a particular aspect of the present invention there is provided a method for detecting a ribosome inhibiting protein, comprising the steps of:

contacting a sample suspected of containing a ribosome inactivating protein with an oligonucleotide substrate having a $GA_xGA$ tetraloop wherein "$A_x$" is a nucleoside comprising an adenine base, derivative or analog thereof; and detecting the presence of the adenine base, derivative or analog thereof released from "$A_x$" of the tetraloop as an indication of the presence of the ribosome inactivating protein in the sample.

In another aspect of the invention, there is provided a reagent for detecting the presence of ribosome inhibiting proteins, the reagent comprising an oligonucleotide substrate including a $GA_xGA$ tetraloop wherein "$A_x$" is a nucleoside comprising a fluorescent adenine derivative or analog base capable of emitting a fluorescence when released from the tetraloop.

In still another aspect of the invention, there is provided an assay kit for detecting the presence of ribosome inactivating protein in an environmental sample, where the assay kit comprises:

an effective amount of an oligonucleotide substrate having a $GA_xGA$ tetraloop wherein "$A_x$" is a nucleoside comprising an adenine base, derivative or analog thereof; and a vessel for retaining a sample suspected of containing a ribosome inactivating protein for contact with the substrate.

The present invention provides a rapid and accurate qualitative and/or quantitative method of detecting RIPs in minute quantities which can be easily carried out in field locations and to assay kits for performing the above method.

BRIEF DESCRIPTION OF THE DRAWINGS

The following drawings are illustrative of embodiments of the invention and are not to be construed as limiting the invention as encompassed by the claims forming part of the application.

DETAILED DESCRIPTION OF THE INVENTION

Figure 1:
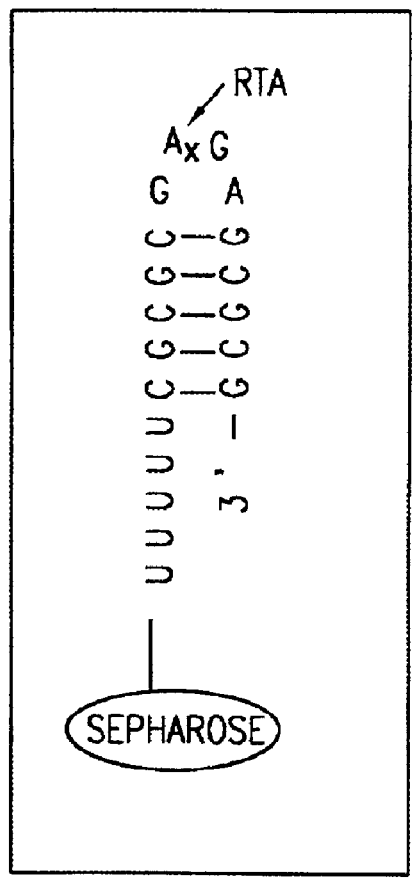
FIG. 1 illustrates the structure of an embodiment of an oligonucleotide substrate, dAU6 20mer (SEQ ID NO: 1) employed in the present invention, attached to a Seqharose solid support with ricin toxin A-chain (RTA), a ribosome inactivating protein, drawn to a specific adenine base, derivative or analog thereof, where an enzymatic base release is initiated.

The present invention is generally directed to a method, a reagent, and an assay kit useful for rapidly detecting the presence of ribosome inactivating proteins (RIPS) particularly Type 2 RIPs and bacterial ribotoxins with similar mechanisms of action as those found in Type 2 RIPs, including, but not limited to, ricin toxin A-chain (RTA), momordin, ricin, abrin-A, gelonin, and SLT-1, in a sample suspected of containing the same. The method of the present invention is adapted for providing rapid and accurate detection of a range of Type 2 RIPs and Type 2-like bacterial ribotoxins, and offering rapid deployability and easy implementation under various environmental conditions as required for military use, for example, under battlefield conditions.

The present invention generally provides a method for detecting the presence of a catalytically active ribosome inactivating protein (RIP) in a sample suspected of containing the same using a nucleic acid or oligonucleotide substrate suspended in a suitable medium or stably attached to a solid support. The term "catalytically active" as used herein means that the ribosome inactivating protein is capable of acting on the nucleic acid substrate at a specific location (i.e. nucleoside), resulting in the release of a specific base which can then be detected.

The term "ribosome inactivating protein" or "ribotoxin" refers to any peptide or polypeptide produced naturally or synthetically which is capable of targeting and enzymatically releasing a specific base located within a specific base sequence in a nucleic acid substrate (i.e. first adenine base of the GAGA tetraloop).

As used herein, the term "nucleotide" refers to a base-sugar-phosphate combination. Nucleotides are the monomeric units of nucleic acid polymers such as DNA and RNA. Included in this definition are modified nucleotides which include additions to the sugar-phosphate groups as well as to the bases. The term "nucleoside" refers to the combination of ribose or deoxyribose and a purine or pyrimidine base connected by a β-N-glycosidic bond therebetween.

The term "nucleic acid" refers to multiple nucleotides attached in the form of a single or double stranded polynucleotide that can be natural, or derived synthetically, enzymatically, and by cloning methods. The term "oligonucleotide" refers to a polynucleotide of less than 75 nucleotides. The terms "nucleic acid" and "oligonucleotide" may be used interchangeably in this application.

The term "fluorescent adenine derivative or analog base" herein refers to any heterocyclic basic amine base including adenine and derivatives and analogs thereof, which possesses or exhibits fluorescent emitting properties for facilitating detection thereof. The fluorescent adenine derivative or analog base may be formed after reacting an adenine base, derivative or analog thereof, released from a nucleic acid substrate with a fluorescent reagent compound.

Alternatively, the fluorescent adenine derivative or analog base may be integrated directly into the nucleic acid substrate prior to being enzymatically released by the RIP. In the latter form, the fluorescent adenine derivative or analog base employed in the present invention is preferably 2-aminopurine. It will be understood herein that any suitable fluorescent adenine derivative or analog base possessing fluorescent emitting properties and capable of being incorporated into an oligonucleotide substrate and being acted upon by a catalytically active RIP for enzymatic release, is intended to be included in the present invention.

The resulting free fluorescent adenine derivative or analog base may then be detectable such as through the use of a fluorescence spectrophotometer or similar measuring apparatus.

Applicants have observed that RIPs invariably target a specific nucleotide sequence specifically the sequence comprising a guanine-adenine-guanine-adenine, or G(A)GA, tetraloop typically found in the large ribosomal RNA of eukaryotic cells. Due to the RIP □s enzymatic specificity, the RIP targets and releases only the first adenine base, (A), of the G(A)GA tetraloop. Through detection of the first adenine base, (A), released from the G(A)GA tetraloop, the presence of RIPs in a sample can readily be established. In this manner, a nucleic acid or oligonucleotide substrate bearing a G(A)GA tetraloop, can effectively function as a simple, reliable assay for detecting the presence of RIPs. It has been further established that the enzymatic base removal process performed by RIPs is sustained even when the adenine base is substituted with an adenine derivative or analog base.

The present invention includes and encompasses all techniques and methods capable of detecting the presence of adenine base, derivative or analog thereof released from a nucleic acid or oligonucleotide substrate. In some embodiments of the present invention, the adenine base, derivative or analog thereof present in (A) may be detectably labeled. The adenine base, derivative or analog thereof of (A) may be labeled with some type of label moiety so as to be detectable by calorimetric, fluorescent, bioluminescent, chemiluminescent, chemifluorescent, electrochemiluminescent, radioisotopic, spectroscopic, photochemical, biochemical, immunochemical, or chemical means. Examples of label moieties include fluorescent dyes, electron-dense reagents, enzymes capable of depositing insoluble reaction products or of being detected chromogenically, such as horseradish peroxidase or alkaline phosphatase, biotin and the like. Radiolabels such as $H_3$, $C_{14}$, $S_{35}$, $P_{32}$, $P_{33}$ and $O_{18}$ may also be incorporated by methods known to those skilled in the art. Furthermore, fluorescent, electroluminescent, chemoluminescent, spin-label, calorimetric, and redox reactive (i.e. for electrochemical detection) groups are commonly employed by those skilled in the art. As will be readily appreciated by workers in the field to which this invention relates, the cleavage of large ribosomal RNA may be readily assessed by various methods well known in the art. Cleavage may, for example, be assessed by running the reaction products (where the substrate is radioactively labeled) on acrylamide, agarose, or other gel systems, and then subjecting the gel to autoradiography or other analytical technique to detect cleavage fragments.

The method for one embodiment of the invention comprises contacting a sample suspected of containing RIPs with an oligonucleotide substrate containing a $GA_xGA$ tetraloop wherein "$A_x$" is a nucleoside comprising an adenine base, derivative or analog thereof, under conditions sufficient to induce enzymatic removal of the corresponding base from "$A_x$". The corresponding base released from "$A_x$" by the RIPs is subsequently treated or modified with a fluorescent reagent compound to yield a fluorescent adenine derivative or analog base. The fluorescent adenine derivative or analog base, is capable of generating about the same signal of known intensity. Thus each positive signal can be tallied in order to obtain quantitative information about the presence of the RIPs (i.e. concentration, rate of catalytic reaction) in the sample.

In principle, any fluorescent reagent compound which possesses high affinity for and reacts specifically with free adenine bases, derivatives and analogs thereof can be used for this determination, as known to those of ordinary skill in the art. The detection of free adenine bases, derivatives and analogs thereof which indicate the presence of RIPs, may be performed using known fluorescence spectrophotometric techniques such as those taught and described in U.S. Pat. No. 3,960,840, the content of which is incorporated herein by reference in its entirety.

Samples suspected of containing RIPs, may include, but not be limited to, air, aerosols, suspension, soil, liquid, water, particles, food, beverages, paste, contact surfaces, fibers, fabrics, clothing, particulates, and the like.

In this embodiment of the present invention, the detectable fluorescent adenine derivative or analog base is prepared by introducing an etheno bridge (—CH=CH—) between the 1 and the $N^6$-positions of the adenine ring present in the non-fluorescent adenine base, derivative of analog thereof, of "$A_x$". The fluorescent adenine derivative or analog base produced by this method emits a fluorescence within the visible spectrum. The fluorescent adenine derivative or analog base is prepared by reacting the non-fluorescent adenine base, derivative or analog thereof, that is released from "$A_x$" of the oligonucleotide substrate by the RIPs, with an acetaldehyde, preferably a haloacetaldehyde selected from the group consisting of chloroacetaldehyde and bromoacetaldehyde, to introduce the 1,$N^6$-etheno bridge into the adenine ring. The reaction takes place readily in solution at a pH within the range of about 1–8, and preferably about 3.5–5.5, and proceeds quantitatively to completion over a period of from about 10 minutes to several hours. The temperature of the reaction is not critical, any temperature above the freezing point of the reaction solution to the boiling point of chloroacetaldehyde and bromoacetaldehyde, respectively, can be used.

The above described fluorescence reaction between the non-fluorescent adenine base, derivatives and analogs thereof and the fluorescent reagent compound may be carried out in the presence of any solvent which is compatible with the reactants. Water is preferred, although organic solvents, such as ethanol, isopropyl alcohol, dimethyl formamide, and acetonitrile, can also be used. The concentration of the solution is similarly not critical and is limited only by the solubility of the reactants in the selected solvent.

Examples of preferred fluorescent reagent compounds include acetaldehydes, more preferably haloacetaldehydes, and most preferably chloroacetaldehyde and bromoacetaldehyde. The preferred fluorescent reagent compounds are not fluorescent, but forms fluorescent adenine derivatives or analog bases, upon reaction with free adenine bases, derivatives and analogs thereof. The resulting fluorescent adenine derivative or analog bases are generally capable of being stimulated at wavelengths in the ultraviolet range, and emitting light at wavelengths in the visible range. It will be understood that the excitation and emission wavelength characteristics of the fluorescent derivatives are not limited as such and may include other wavelength characteristics.

In a preferred embodiment of the present invention, the method comprises contacting a sample suspected of containing RIPs with an oligonucleotide substrate containing a $GA_xGA$ tetraloop wherein "$A_x$" is a nucleoside comprising a fluorescent adenine derivative or analog base, preferably 2-aminopurine, under conditions sufficient to induce enzymatic removal of corresponding fluorescent base from "$A_x$". In this embodiment, the fluorescent reagent compound treating step described above is effectively eliminated, since the fluorescent adenine derivative or analog base of "$A_x$" automatically fluoresces upon release for efficient detection. The released fluorescent adenine derivative or analog base may be readily detected using conventional fluorescence measuring apparatuses. The fluorescent adenine derivative or analog base may be incorporated into the oligonucletide substrate as known to those of ordinary skill in the art, during the chemical synthesis of the substrate, during post-synthetic modification of the substrate, or during enzymatic synthesis or modification of the substrate.

The method of the present invention for detecting enzymatic activity of RIPs may optionally include steps for separating products (i.e., free or released adenine base, derivative or analog thereof before quantification. It will be understood that in some cases the absorbance spectra of reactants and products may be similar or identical. A technique for separating and identifying reactants and products may be incorporated and applied to improve signal detection resolution as known by those skilled in the art. By way of example, the resolution of products could be accomplished through the use of techniques including, but not limited to, high-pressure liquid chromatography (HPLC), microbore, capillary liquid chromatography, capillary electrophoresis, spin column separation technology, and the like.

By way of further example, the oligonucleotide substrates of the present invention may be fixed or stably attached to an activated portion of a solid support as known to those of ordinary skill in the art. In this manner the substrate is immobilized during release of the fluorescent or non-fluorescent adenine base, derivative or analog thereof from "$A_x$". The released adenine bases, derivatives or analogs thereof can subsequently be extracted in a optionally suitable manner, particularly if non-fluorescent, via a spin column apparatus, for example, for signal detection. Extraction step or techniques is not necessary for signal detection where the released adenine base, derivative or analog thereof is fluorescent. The immobilization of the oligonucleotide substrates can also be carried out in accordance with any method known in the art for example, with the aid of a cross-linking agent, by trapping the oligonucleotide substrate between two porous membranes which permit passage of smaller molecules, and the like. The step of affixing or attaching the oligonucleotide substrate to the surface of a solid support serves to improve signal detection, resolution and noise reduction in the assay.

The methods of the present invention are based on the fact that RIPs enzymatically act upon the large ribosomal RNA in cells of eukaryotic origin at a specific site, yielding released adenine bases, whereby the amount of adenine bases released may be measured to extrapolate the amount of RIPs present in the sample. By way of example, each oligonucleotide substrate may be constructed to include one $GA_xGA$ tetraloop whereby one mole of adenine base, derivative or analog thereof, is released from every mole of oligonucleotide substrate that is cleaved by the RIPs. The extent or rate of cleavage can then be measured by determining the amount of, or rate of appearance of, released adenine bases, derivative or analog thereof. The concentration of the RIP in an unknown sample can then be calculated, based on measurements of the extent or rate of release, effected by known concentrations of the RIP.

Referring to FIG. 1, an oligonucleotide substrate for one embodiment of the present invention comprises a plurality of nucleotides attached in the form of a single or double stranded polynucleotide, and a $GA_xGA$ tetraloop wherein "$A_x$" is a nucleoside comprising a fluorescent adenine derivative or analog base. In this embodiment, the fluorescent adenine derivative or analog base is preferably 2-aminopurine. As shown in FIG. 1, the $GA_xGA$ tetraloop is formed by the oligonucleotide substrate through hybridization of a series of bases attached at one end of the $GA_xGA$ sequence with a corresponding complementary series of bases attached at the other end to yield a chain of multiple hybridized base pairs. A sample suspected of containing an RIP is contacted with the oligonucleotide substrate bearing the $GA_xGA$ tetraloop. The RIP, if present, selectively cleaves the N-glycosidic bond and releases the fluorescent adenine derivative or analog base from the nucleoside, "$A_x$" of the $GA_xGA$ tetraloop to yield a detectable compound. The detectable compound fluoresces or emits electromagnetic radiation, preferably visible light, when stimulated via the absorption of an incident radiation. The resulting emitted fluorescence may persist only as long as the stimulating radiation is continued. The detectable fluorescent adenine derivative or analog base when detected is indicative of the presence of the RIP in the sample.

As described above, the released fluorescent adenine derivative or analog base emits a detectable fluorescent signal continuously or when stimulated with an incident or excitation electromagnetic radiation. Each individual fluorescent adenine derivative or analog base released from the $GA_xGA$ tetraloop is capable of generating about the same signal of known intensity. Thus each positive signal can be tallied in order to obtain quantitative information about the presence of the RIPs (i.e. concentration, rate of catalytic reaction) in the sample.

In the present invention, the fluorescent adenine derivative or analog base may generally be capable of being stimulated at wavelengths in the ultraviolet range, and emitting light at wavelengths in the visible range in response to the excitation electromagnetic radiation. It will be understood that the excitation and emission wavelength characteristics of the fluorescent base compounds are not limited as such and may include other wavelength characteristics.

Nucleotides represented in the oligonucleotide substrates of the present invention generally comprise a sugar, base and a phosphate group or a phosphodiester linkage. It will be understood that the portions of the oligonucleotide substrates used in the present invention will contain the conventional bases adenine, guanine, cytosine, and uracil. Included within the invention are oligonucleotide substrates which are formed from synthetic procedures incorporating analogous forms of purines and pyrimidines. Accordingly, nucleotide derivatives or modifications may be made at the level of the sugar, base, phosphate groupings or phosphodiester linkages for modifying stability, signal strength and resolution, operating and shelf life, incidences of false signals, sensitivity, and the like.

In one embodiment of this invention, the sugar of the nucleotide may be a ribose or deoxyribose such that the nucleotide is either a ribonucleotide or a deoxyribonucleotide, respectively. The oligonucleotide substrate of the present invention may be composed of ribonucleotides or a combination of ribonucleotides and deoxyribonucleotides. The sugar moiety of the nucleotide may be further modified according to well known methods in the art. The invention is preferably directed to compounds with a substituted 2' hydroxyl such as 2'-O-methyl.

In a preferred embodiment of the present invention, a 2'-O-methylated oligonucleotide substrate, a synthetic form of a nucleic acid containing modified nucleotides, comprising a $GA_xGA$ tetraloop, is utilized. The 2'-O-methylated oligonucleotide substrate may be stably fixed on a solid support or suspended in a medium. The 2'-O-methylated oligonucleotide substrate is highly resistant to nucleases and enzymes capable of hydrolyzing phosphodiester bonds, and is also resistant to highly alkaline moieties and conditions for greater stability and lower noise signal generation. The nucleases, enzymes, and alkaline moieties may be present as contaminants in a sample to be assayed. Such chemical resistance and stability makes the 2'-O-methylated oligonucleotide substrates especially suitable for conditions existing especially in the field. Synthesis of such oligonucleotides with the modified bases and sugars may be carried out using methods known to those of ordinary skill in the art.

Preferred forms of oligonucleotide substrates include 2'-O-methylated ribonucleic acid substrates such as a 14-mer with a $GA_xGA$ tetraloop wherein "$A_x$" is a deoxyribonucleoside comprising a fluorescent adenine derivative or analog base (2'-O-Me7dA 14-mer). As shown best in FIG. 1, the 2'-O-Me7dA 14-mer is attached through suitable means to a solid matrix or support for constructing an effective assay. The 2'-O-Me7dA 14-mer further includes six uracil bases forming a spacer between the 5' end of the oligonucleotide substrate and the support. The oligonucleotide substrate is attached to a Sepharose support media via an amino-link at the 5' end thereof. The oligonucleotide substrate comprises fourteen heterocyclic amine bases and six spacer bases. The nucleic acid sequence is formed by hybridizing the five amine bases at one end of the tetraloop sequence with five complementary bases at the other end, to form a unhybridized loop of four bases, $GA_xGA$. The loop referred to as a tetraloop, comprises the following base sequence: $GA_xGA$, wherein "$A_x$" is a deoxyribonucleoside comprising a fluorescent adenine derivative or analog base, including, but not limited to, 2-aminopurine. The A and G are each a nucleoside comprising an adenine base and guanine base, respectively. The resulting oligonucleotide substrate attached to the solid support yields a 2'-O-Me7dA 20mer, or referred herein as "dAU6 20mer" the structure of which is shown in FIG. 1.

As noted above, RIPs have an affinity for a specific nucleic acid sequence (i.e., GAGA tetraloop) found in large ribosomal RNA in eukaryotic cells. The dAU6 20mer substrate includes the $GA_xGA$ tetraloop wherein "$A_x$" is a nucleoside comprising a fluorescent adenine derivative or analog base, which enables rapid detection for the presence of RIPs such as RTA, momordin, abrin-A, gelonin, SLT-1, and the like, in air. It will be understood that those of ordinary skill in the art will recognized that different nucleic acid sequences which comprises at least one $GA_xGA$ tetraloop may be suitably used for the detection of RIPs and are within the scope of this invention. Accordingly, detection of any RIP which targets the $GA_xGA$ tetraloop for cleavage and release of a fluorescent adenine derivative or analog base such as 2-aminopurine, is encompassed within the scope of the present invention.

All nucleic acid sequences described above are adapted for use in an assay to measure the presence of RIPs in a given environmental sample. Such an assay may be performed in the following manner as described. A plurality of dAU6 20mer substrates are attached to a Sepharose solid support by coupling the oligonucleotide substrate with an NHS-activated portion of the Sepharose support at 4° C. The substrate and support is maintained at the temperature for about 18 hours. Any non-reacted dAU6 20mer groups that remain unattached on the solid support is blocked by Tris buffer (1.0M, pH 7.40) for 3 hours. The Sepharose support with the dAU6 20mer is then pre-packed into a spinning mini-column available from vendors such as QIAGEN (Valencia, Calif.), or PROMEGA (Madison, Wis.).

A sample containing a quantity of RIP is mixed thoroughly with 100 μl of 20 mM potassium acetate and 1 mM EDTA at pH 4.0, to yield a sample solution. The sample solution is then added to the column containing the dAU6 20mer treated Sepharose support. The column is incubated for 5 to 10 minutes at about 37° C. The dispensing end of the column is put into a collecting tube (e.g., 1.5 mL Eppendorf tube). The column and tube are then centrifuged for 30 seconds at maximum acceleration. (Alternatively, a syringe or similar apparatus may be used to create a positive pressure at the receiving end of the column to expel the sample solution from the column into the collecting tube.) The resulting filtrate is collected. A fluorescence spectrophotometer is utilized for measuring the fluorescence with the excitation and emission filters set at about 275 nm and 417 nm, respectively. The assay procedure described above is capable of detecting 16 pmol of RIP in a span of time of less than 15 minutes.

It will be understood that the embodiment previously described with the use of a oligonucleotide 14mer having a 2'-deoxyribonucleoside at position 7 attached to a Sepharose solid support is disclosed for illustrative purposes. Those skilled in the art will recognize that any nucleic acid substrate containing a $GA_xGA$ tetraloop where "$A_x$" is a ribo- or deoxyribonucleoside comprising a fluorescent adenine derivative or analog base, may be used to detect RIPs in the present invention. Additionally, the oligonucleotide 14mer may be attached to any suitable solid support as known to those skilled in the art.

The present invention provides for a RIP detection assay kit for performing the methods of the present invention described above using the oligonucleotide substrates of the present invention. The assay kit of the present invention includes all the necessary reagents and vessels for the detecting the presence of RIPs in a given environmental sample. Accordingly, the assay kit contains a sufficient amount of an oligonucleotide substrate including a $GA_xGA$ tetraloop wherein "$A_x$" is a nucleoside comprising a fluorescent adenine derivative or analog base which may be enzymatically released from "$A_x$" by RIPs for subsequent detection.

The assay kit may also comprise one or more vessels or receptacles useful for accommodating sufficient amounts of the oligonucleotide substrates of the present invention to carry out the method of the present invention, instructions for implementation, and optionally, and optionally, the fluorescent reagent compounds. The "instructions for implementation" includes any tangible expression describing the fluorescent reagent compound and the oligonucleotide substrate concentration for at least one method of the present invention, parameters such as the relative amounts of oligonucleotide substrate and sample to be admixed, maintenance time periods for substrate/sample admixtures, temperature, buffer conditions, pH levels, and the like.

After collecting an environmental sample, detection of RIPs via signals may be effected with a suitable fluorescence measurement apparatus which is optionally included in the assay kit of the present invention. Preferably, the fluorescence measurement apparatus is portable with a suitable size and weight for field use.

In one form of the assay kit, a oligonucleotide substrate of the present invention, may be fixed or attached to a gene chip where a reader device is used to detect free adenine derivative bases through techniques known to those of ordinary skill in the art. Alternatively, the substrate may be attached to a strip comprising a cellulose or plastic material. The cellulose or plastic strip containing the oligonucleotide substrate of the present invention may be contacted with a sample suspected of containing RIPs for a suitable time interval and analyzed using portable fluorescence detectors for detecting the presence of the RIPs. Suitable apparatuses may be used for collecting various forms of substances capable of harboring or containing the RIPs. By way of example, air samplers may be used to collect and concentrate samples from the air through techniques known to those of ordinary skill in the art.

The foregoing discussion discloses and describes merely exemplary embodiments of the present invention. One skilled in the art will readily recognize from such discussion, and from the accompanying drawings, examples and claims, that various changes, modifications and variations can be made therein without departing from the spirit and scope of the invention as defined in the following claims.

EXAMPLE 1

A number of oligonucleotide substrates comprising a deoxyadenosine nucleoside attached to Sepharose, were prepared for this study. The dA 20mer oligonucleotides were attached to Sepharose by coupling the oligonucleotide substrate with an NHS-activated portion of the Sepharose support at 4° C. The substrate and support is maintained at the temperature for about 18 hours. Any non-reacted dA 20mer groups that remain unattached on the solid support is blocked by Tris buffer (1.0M, pH 7.40) for 3 hours. There were three groups of amino-linked oligonucleotide substrates with a deoxyadenosine nucleoside: a spacer comprising 3 uracil bases (dAU3NH3), a spacer comprising 6 uracil bases (dAU6NH3), and a spacer comprising 9 uracil bases (dAU9NH3), respectively. A negative control was also prepared comprising an oligonucleotide substrate with no spacer (dANH3).

Each group was tested for ricin toxin A-chain (RTA) depurination. For each group, 1.0 nmol of the oligonucleotide substrate was added to a solution containing 20 µl of 20 mM potassium acetate and 1 mM EDTA at a pH of 4 to yield a reaction mixture. 16 pmol of RTA was then added to each of the reaction mixtures excluding the control, and incubated at 37° C. for about 10 minutes. Each reaction mixture was diluted with equal volume of distilled water. For each of the reaction mixtures, the resulting free adenine or adenine derivative base groups cleaved, was isolated and purified by Microcon-3 filtration, from AMICON (Danvers, Mass.). The filter apparatus was spun at a rate of acceleration of about 14,000 g for about 30 minutes. 20 µL of filtrate from each reaction mixture, was collected and treated with 1.0 µL of 4M bromoacetaldehyde. The BAA treated filtrates were incubated at 95° C. for about 10 minutes. The filtrates were each diluted with 880 µL of distilled water. The fluorescence was measured using a Perkin-Elmer 650-10S fluorescence spectrophotometer with filters set at an excitation wavelength of about 275 nm and an emission wavelength of about 417 nm.

Figure 2:
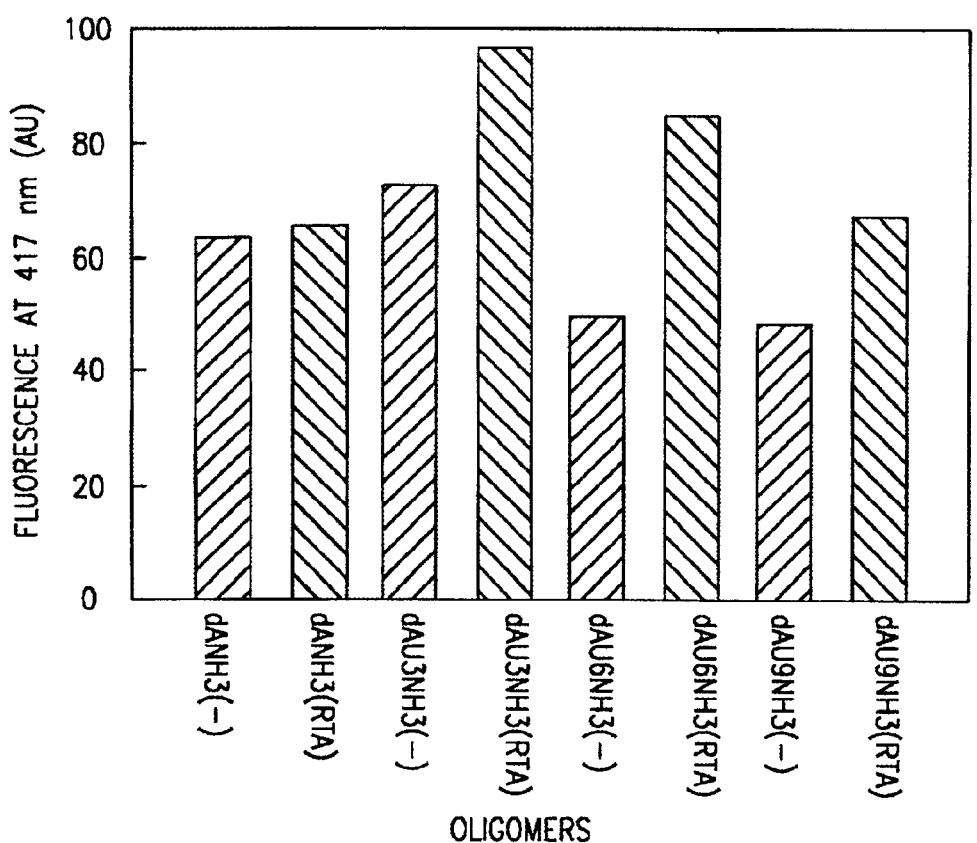
FIG. 2 is a graph illustrating fluorescence determinations in RTA samples using four different amino-linked oligonucleotide substrates.

The results are shown and summarized in FIG. 2. All four groups of oligonucleotide substrates tested showed in view of the corresponding negative controls, varying levels of depurination activity, with the dAU6 20mer or dAU6NH3 (6 uracil base spacer oligonucleotide) showing greater detection effectiveness.

EXAMPLE 2

The dAU6 NH3 oligonucleotide substrates were prepared and attached to Sepharose in the manner described in Example 1. 6 RIP samples were prepared and tested. The samples comprised no RIPs, RTA, momordin, abrin-A, gelonin, and SLT-1. Excluding the negative control, 16 pmol of an RIP was mixed with a solution containing 1.0 nmol of oligonucleotide substrate suspended in 20 µL of 20 mM potassium acetate and 1 mM EDTA at a pH of about 4.0. to yield a reaction mixture The reaction mixtures were incubated at 37° C. for about 10 minutes. The samples were each diluted with equal volume of distilled water. For each of the reaction mixtures, the resulting free adenine or adenine derivative base groups cleaved, was isolated and purified by Microcon-3 filtration which was spun at a rate of acceleration of about 14,000 g for about 30 minutes.

Figure 3:
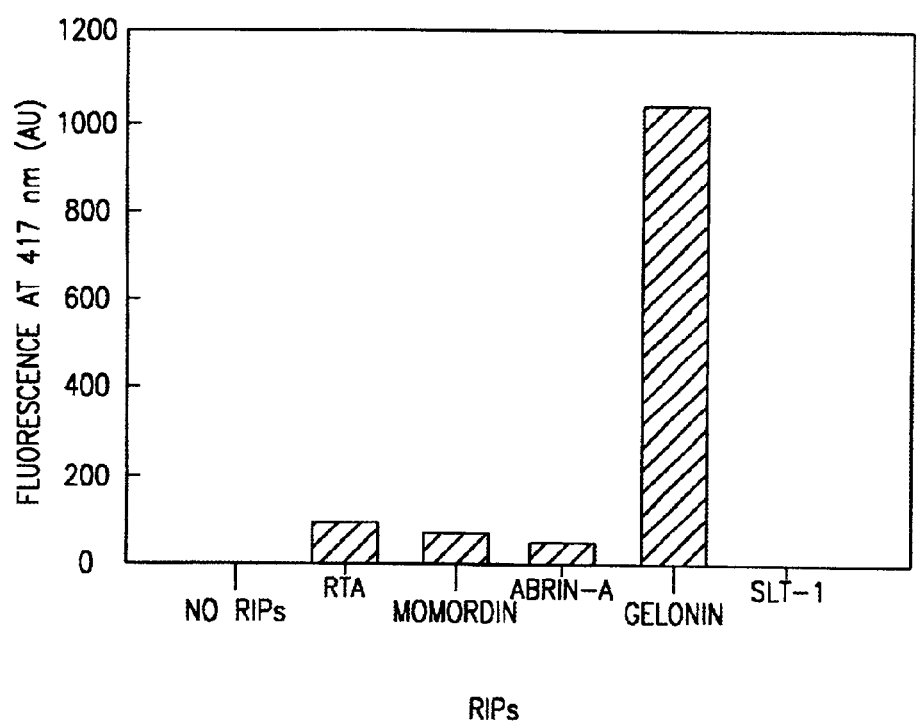
FIG. 3 is a graph illustrating fluorescence determinations in five RIP samples and one negative control sample using an amino-linked oligonucleotide substrate.

20 µL of filtrate was collected from each reaction mixture and treated with 1.0 µL of 4 M bromoacetaldehyde. The treated filtrate was incubated at 95° C. for about 10 minutes. Each of the samples were diluted with 880 µL of distilled water and the fluorescence was measured in the same manner described in Example 1. The results are shown in FIG. 3. The results corresponding with the RIPs, were normalized with the negative control (no RIPs). The gelonin sample produced the highest level of activity and the SLT-1 elicited no detectable activity.

EXAMPLE 3

A plurality of oligonucleotide substrates, dAU6 NH3 20mer were prepared and attached to a Sepharose solid support. The oligonucleotide substrate was attached to the Sepharose solid support through coupling between the 5' end of the substrate and an NHS-activated portion of the Sepharose support at a temperature of about 4° C. for about 18 hours. The unattached oligonucleotide substrates were blocked in Tris buffer (1.0 M, pH 7.4) for about 3 hours to yield a substrate equilibrate.

Two samples were prepared for the experiment. The first sample was prepared by adding 16 pmol of RTA to 50 µL of 20 mM potassium acetate, 1 mM EDTA at a pH of about 4.0. The second sample was prepared in the same manner without the RTA. The samples were each added to the substrate equilibrate in the presence of 50 µL of 20 mM potassium acetate and 1 mM EDTA at a pH of about 4.0.

The resulting substrate equilibrate were each incorporated into a QIA quick spin column from QIAGEN (Velencia, Calif.). The columns were incubated at 37° C. for about 10 minutes and then centrifuged at an acceleration rate of about 14,000 g for about 1 minute. Each of the columns yielded about 100 µL of filtrate. The filtrates were then treated with 5.0 µL of 4 M bromoacetaldehyde and incubated at 95° C. for about 10 minutes. The treated filtrates were each diluted with 880 µL of distilled water and the fluorescence was measured in the same manner described in Example 1.

Figure 4:
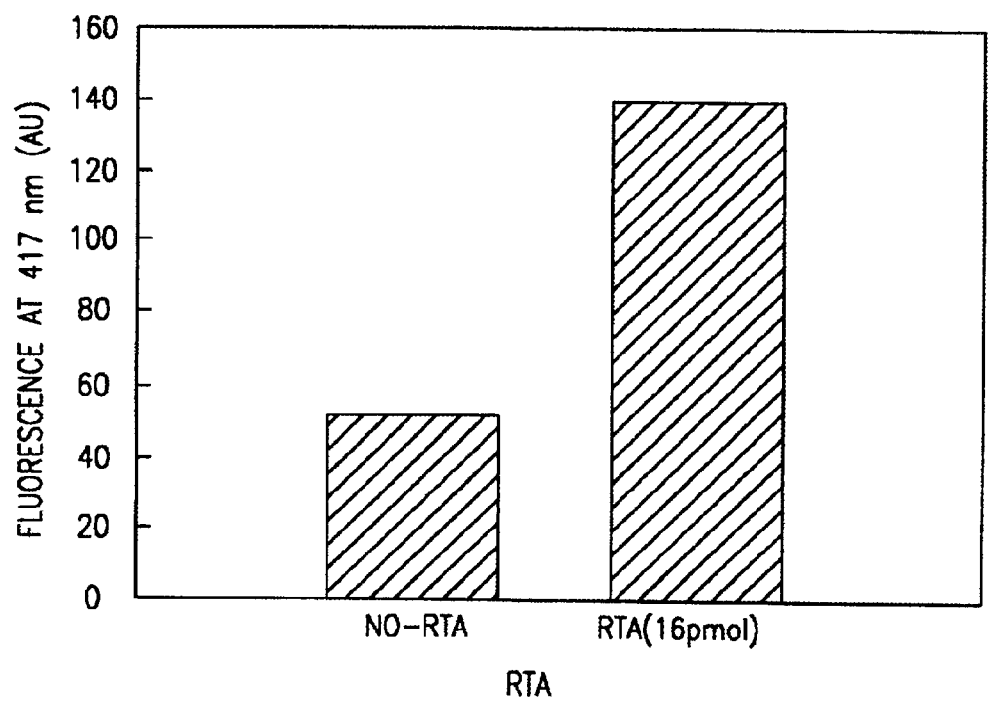
FIG. 4 is a graph illustrating fluorescence determinations in a RTA sample and a negative control sample using an amino-linked oligonucleotide substrate attached to a solid support.

As shown in FIG. 4, the sample containing RTA cleaved and released adenine from the oligonucleotide polymer substrates, and was detected by fluorescence spectophotometry at a higher intensity than the sample without RTA.

EXAMPLE 4

A synthetic 2'-O-methylated oligonucleotide 14mer substrate containing a $GA_xGA$ tetraloop where "$A_x$" is a deoxyribonucleoside comprising a 2-aminopurine base, was tested with RTA. A reaction mixture was prepared with varying concentrations of RTA. The reaction mixtures each contained 2.91 µM of the 14mer substrate, 10 mM of sodium acetate, 1 mM of EDTA at a pH of about 4.0 and concentrations of RTA at 3.13 nM, 12.5 nM, 25 nM, 50 nM, and 100 nM, respectively. The reaction mixtures were incubated at about 37° C. for about 10 minutes. The fluorescence of the released 2-aminopurine was measured with a Perkin-Elmer fluorescence spectrophotometer Model No. LS50B with an excitation wavelength filter set at 310 nm and an emission wavelength filter set at 370 nm.

Figure 5:
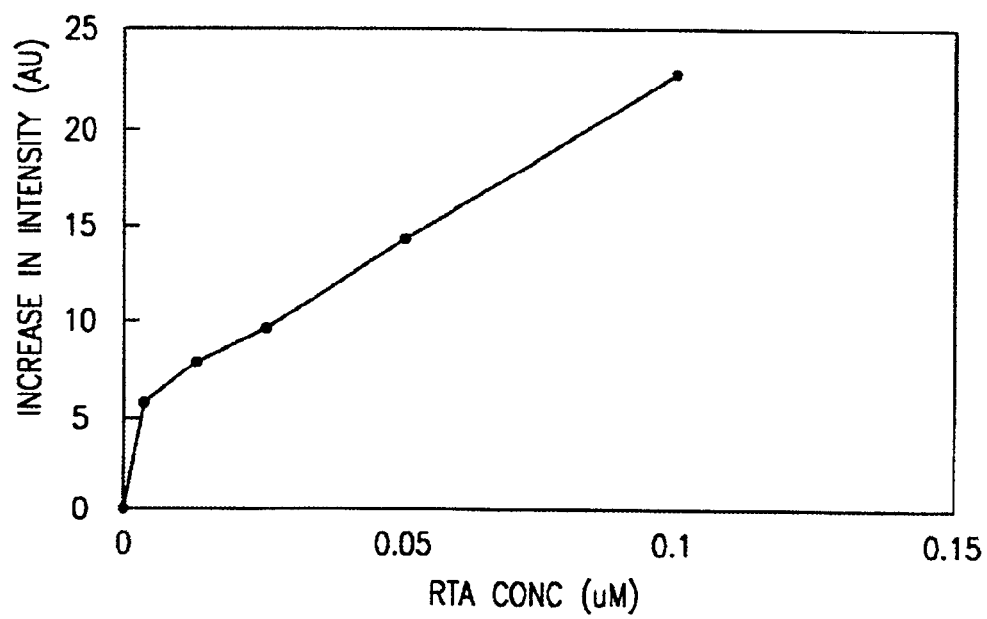
FIG. 5 is a graph illustrating fluorescence determinations in RTA samples at various concentrations using a synthetic 2'-O-methylated oligonucleotide 14mer substrate containing a $GA_xGA$ tetraloop where "$A_x$" is a deoxyribonucleoside comprising a 2-aminopurine base.

The results shown in FIG. 5 indicate that the rate of 2-aminopurine base release is dependent on the concentration of the RTA present in the sample.

EXAMPLE 5

A synthetic 2'-O-methylated oligonucleotide 14mer substrate containing a $GA_xGA$ tetraloop where "$A_x$" is a deoxyribonucleoside comprising a 2-aminopurine base, was tested with RTA. A reaction mixture was prepared for each of six time intervals of incubation. The reaction mixtures were prepared and each contained 20.5 µM of the 14mer substrate, 10 mM of sodium acetate, 1 mM of EDTA at a pH of about 4.0 and 500 nmol of RTA. The reaction mixtures were each incubated at about 37° C. at varying time intervals as shown a graphical plot in FIG. 6.

A high-pressure liquid chromatography (HPLC) of each of the reaction mixtures was performed using an HP Hypersil BDS-C18 (25 cm×4.6 cm) column with a particle size of 5 µm, a flow rate of 1 mL/minute, and a pressure of 175 psi. Each of the reaction mixtures was passed at a column temperature of about 30° C. using an isocratic elution containing 10% MeOH-90% $NH_4OAc$ at a pH of about 5.2. The retention time of the 2-aminopurine was about 5.4 minutes and 3.05 minutes for the oligonucleotide 14-mer. The fluorescence transmitted by the released 2-aminopurine base was measured with a Hewlett Packard HPLC 1100 system equipped with a diode array and fluorescence detectors.

Figure 6:
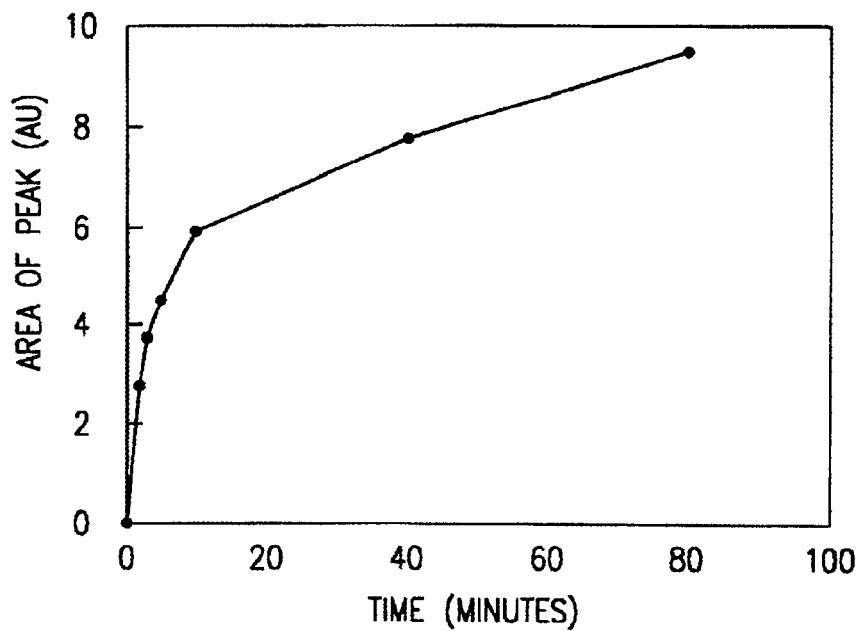
FIG. 6 is a graph illustrating fluorescence determinations in RTA samples at various incubation time intervals using a synthetic 2'-O-methylated oligonucleotide 14mer substrate containing a $GA_xGA$ tetraloop where "$A_x$" is a deoxyribonucleoside comprising a 2-aminopurine base.

The results are shown in FIG. 6 which indicate that the presence of the RTA toxin can be detected in about 2 minutes.

What is claimed is:

1. A method for the qualitative and/or quantitative detection of a ribosome inactivating protein, comprising:
   contacting a sample suspected of containing a ribosome inactivating protein having N-glycosidase activity with an oligonucleotide substrate having a GA$_x$GA tetraloop wherein "A$_x$" is a nucleoside comprising an adenine analog 2-aminopurine; and
   detecting the presence of the adenine analog thereof released from "A$_x$" of said tetraloop as an indication of the presence of the ribosome inactivating protein in the sample.

2. The method of claim 1, wherein the adenine analog 2-aminopurine is capable of immediately emitting fluorescence when released from said tetraloop.

3. The method of claim 1, wherein the oligonucleotide substrate comprises 2'-O-methylated nucleosides.

4. The method of claim 3, wherein the 2'-O-methylated oligonucleotide substrate is attached to a solid support.

5. The method of claim 3, wherein the GA$_x$GA tetraloop comprises deoxyribonucleosides.

6. The method of claim 3, wherein the "A$_x$" of the GA$_x$GA tetraloop comprises a deoxyribonucleoside.

7. The method of claim 4, wherein the solid support is Sepharose.

8. The method of claim 2, further comprising detecting the presence of the fluorescent adenine analog base 2-aminopurine of "A$_x$" using fluorescence spectrometry.

* * * * *